United States Patent
Kody et al.

(10) Patent No.: US 9,503,282 B2
(45) Date of Patent: Nov. 22, 2016

(54) METHODS AND SYSTEMS FOR DETERMINING THE POSITIONS OF ORTHODONTIC APPLIANCES

(75) Inventors: Robert S. Kody, Woodbury, MN (US); David W. Kuhns, Monrovia, CA (US); Richard E. Raby, Lino Lakes, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 7 days.

(21) Appl. No.: 13/063,967

(22) PCT Filed: Sep. 8, 2009

(86) PCT No.: PCT/US2009/056229
§ 371 (c)(1),
(2), (4) Date: Sep. 1, 2011

(87) PCT Pub. No.: WO2010/033404
PCT Pub. Date: Mar. 25, 2010

(65) Prior Publication Data
US 2011/0306003 A1 Dec. 15, 2011

Related U.S. Application Data

(60) Provisional application No. 61/098,336, filed on Sep. 19, 2008.

(51) Int. Cl.
*A61C 7/14* (2006.01)
*H04L 12/58* (2006.01)
*H04N 1/00* (2006.01)

(52) U.S. Cl.
CPC ......... *H04L 12/5835* (2013.01); *H04L 51/066* (2013.01); *H04N 1/00212* (2013.01);
(Continued)

(58) Field of Classification Search
CPC .............. A61C 7/00; A61C 7/002; A61C 7/14
(Continued)

(56) References Cited

U.S. PATENT DOCUMENTS 5,395,238 A * 3/1995 Andreiko et al. .............. 433/24
5,431,562 A * 7/1995 Andreiko et al. .............. 433/24
(Continued)

FOREIGN PATENT DOCUMENTS

| JP | H05-261124 | 10/1993 |
| JP | H08-507174 | 9/1996 |
| WO | WO 97-03622 | 2/1997 |

OTHER PUBLICATIONS

Kalange, "Prescription Full Arch Indirect Bonding Utilizing Adhesive Precoated Brackets", Orthodontic Perspectives, A 3M Unitek Publication, vol. VII, No. 1, 2001, pp. 7, 10-11.
(Continued)

*Primary Examiner* — Matthew Nelson
(74) *Attorney, Agent, or Firm* — Kevin Weber

(57) ABSTRACT

The positions of orthodontic appliances such as brackets and buccal tubes on a patient's teeth are determined using digital data that represents the shapes of the patient's teeth. Certain landmarks of the teeth such as the marginal ridges are determined using software, and the software adjusts positions of the virtual appliances on the teeth as needed in order to bring the marginal ridges into proper alignment at the conclusion of treatment. The resulting positions are optionally used to determine the location of the appliances in an indirect bonding apparatus such as a transfer tray.

19 Claims, 6 Drawing Sheets

(52) U.S. Cl.
CPC ...... *H04N 1/00214* (2013.01); *H04N 1/00217* (2013.01); *H04N 1/00312* (2013.01); *H04N 1/00281* (2013.01); *H04N 2201/0094* (2013.01)

(58) Field of Classification Search
USPC .................... 433/24, 8–17; 700/118; 703/11
See application file for complete search history.

(56) References Cited

U.S. PATENT DOCUMENTS

| | | |
|---|---|---|
| 5,474,448 A | 12/1995 | Andreiko et al. |
| 5,533,895 A | 7/1996 | Andreiko et al. |
| 6,733,289 B2 | 5/2004 | Manemann |
| 7,033,327 B2 | 4/2006 | Raby |
| 7,155,373 B2 | 12/2006 | Jordan |
| 7,210,929 B2 | 5/2007 | Raby |
| 7,291,011 B2 | 11/2007 | Stark |
| 2004/0214128 A1* | 10/2004 | Sachdeva et al. ............. 433/24 |
| 2005/0170309 A1 | 8/2005 | Raby |
| 2005/0271996 A1 | 12/2005 | Sporbert |
| 2006/0024637 A1* | 2/2006 | Raby et al. .................... 433/24 |
| 2006/0073436 A1 | 4/2006 | Raby |
| 2006/0084030 A1* | 4/2006 | Phan et al. ..................... 433/72 |
| 2006/0099545 A1 | 5/2006 | Lai |
| 2006/0263739 A1* | 11/2006 | Sporbert et al. ............... 433/24 |
| 2007/0141526 A1 | 6/2007 | Eisenberg |
| 2007/0218418 A1* | 9/2007 | Raby et al. .................... 433/24 |
| 2007/0238064 A1 | 10/2007 | Stark |

OTHER PUBLICATIONS

International Search Report for PCT/US2009/056299, mailed Dec. 11, 2009, 4 pages.

* cited by examiner

METHODS AND SYSTEMS FOR DETERMINING THE POSITIONS OF ORTHODONTIC APPLIANCES

CROSS REFERENCE TO RELATED APPLICATIONS

This application is a national stage filing under 35 U.S.C. 371 of PCT/US2009/056299, filed Sep. 9, 2009, which claims priority to U.S. Application No. 61/098,336, filed Sep. 19, 2008, the disclosure of which is incorporated by reference in its/their entirety herein.

BACKGROUND OF THE INVENTION

1. Field of the Invention

This invention relates to methods and systems for determining positions of a number of orthodontic appliances on respective teeth of a patient's dental arch.

2. Description of the Related Art

The field of orthodontics is concerned with repositioning and aligning a patient's teeth for improved occlusion and aesthetic appearance. Orthodontic treatment often involves the use of tiny slotted appliances known as brackets that are fixed to the patient's anterior, canine, and bicuspid teeth. An archwire is received in the slot of each bracket and serves as a track to guide movement of the teeth to desired orientations. The ends of the archwire are usually received in appliances known as buccal tubes that are secured to the patient's molar teeth.

A number of orthodontic appliances in commercial use today are constructed on the principle of the "straight wire concept" developed by Dr. Lawrence F. Andrews, D.D.S. In accordance with this concept, the shape of the appliances, including the orientation of the slots of the appliances, is selected so that the slots are aligned in a flat reference plane at the conclusion of treatment. Additionally, a resilient archwire is selected with an overall curved shape that lies in a flat reference plane when relaxed.

When the archwire is placed in the slots of the straight wire appliances at the beginning of orthodontic treatment, the archwire is often deflected upwardly or downwardly from one appliance to the next in accordance with locations of the maloccluded teeth in the patient's dental arch. However, the resiliency of the archwire tends to return the archwire to its normally curved shape that lies in a flat reference plane. As the archwire shifts toward the flat reference plane, the attached teeth are moved in a corresponding fashion toward an aligned, aesthetically pleasing array.

As can be appreciated, it is important for the practitioner using straight wire appliances to fix each bracket in the exact proper position on the corresponding tooth. If, for example, a bracket is placed too far in an occlusal direction on the tooth surface, the archwire will tend to position the crown of the tooth too close to the gingiva (gums) at the end of the treatment. As another example, if the bracket is placed to one side of the center of the tooth in either the mesial or distal direction, the resultant tooth orientation will likely be an orientation that is excessively rotated about its long axis.

The process of positioning and bonding the appliances to the patient's teeth requires considerable care, and the practitioner often must visually determine the proper location of the brackets on the respective teeth. In a technique known as indirect bonding, a practitioner often determines appliance positions by the use of a ruler, protractor and pencil to measure and mark features on a plaster cast made from impressions of the patient's teeth. However, this process is somewhat time-consuming and difficult to carry out with precision, and may be subjective in nature. Consequently, it is often difficult for the practitioner to ensure that the brackets are precisely positioned on the teeth at correct locations.

SUMMARY OF THE INVENTION

In general, the present invention is directed toward methods and systems for positioning orthodontic appliances on teeth that take into account certain structural features of patient-specific teeth as well as the practitioner's preferred treatment methodology. The present invention involves the use of digital data files representing the shapes of teeth for determining marginal ridges, and software is utilized to calculate a set of proposed appliance heights relative to the corresponding marginal ridges for each appliance in the dental arch so that the marginal ridges are properly aligned at the conclusion of treatment.

As one option, the orthodontic practitioner may select a standardized appliance placement protocol wherein the desired height of each appliance has been selected based on past experience and/or recommendations of other practitioners in the orthodontic field. In general, such appliance heights in the past have been based upon the distances of the appliances from the cusp tips or incisal edges of the corresponding tooth. However, by use of a digital data file that is representative of the shapes of an individual patient's teeth, the location of the marginal ridges can be precisely determined using software. The software can calculate a set of new appliance heights based on adjustments of the original set of appliance heights that are necessary in order to ensure that the marginal ridges are in proper alignment once the archwire has shifted toward the flat reference plane at the conclusion of treatment.

In more detail, the present invention in one aspect relates to a method of determining the position of orthodontic appliances that comprises the acts of obtaining a digital data file representative of the shapes of teeth of a dental arch, and using the digital data file to determine marginal ridge heights of a first tooth and a second tooth of the dental arch. The method further comprises the acts of selecting an appliance height for the first tooth of a dental arch and determining the distance between the selected appliance height for the first tooth and the marginal ridge height of the first tooth. The method also includes the act of proposing an appliance height for the second tooth at a distance from the marginal ridge height of the second tooth that is based on the determined distance.

Another aspect of the invention is also directed toward a method of determining the position of orthodontic appliances. This method comprises the act of obtaining a digital data file that represents the shapes of teeth of a dental arch, and the act of using the digital data file to determine data representing the marginal ridge height of one tooth of the dental arch. This method further comprises the acts of determining the difference between the marginal ridge height and the occlusal plane height of the tooth, and using the determined difference to propose appliance heights for at least one remaining tooth of the dental arch.

An additional aspect of the present invention is also directed to a method of determining the position of orthodontic appliances. This method includes the acts of obtaining a digital data file that represents the shapes of teeth of a dental arch and using the digital data file to determine a marginal ridge height of a molar tooth and the marginal ridge height of a premolar tooth that is located in the same quadrant as the molar tooth. This method further includes the act of selecting an appliance height for the molar tooth and an appliance height for the premolar tooth that are spaced approximately the same distance from the marginal ridge height of the molar tooth and the premolar tooth respectively.

The present invention is a significant advantage in that the digital data file can be used with software to quickly and accurately define marginal ridge heights of the patient's teeth. Such ridge heights are difficult and time consuming to determine using manual measurement techniques, and the complex three-dimensional geometry of the teeth make it very difficult for the average practitioner to arrive at precise and repeatable results using manual techniques. Furthermore, a substantial portion of the methods of the present invention can be delegated to the technician, representing a savings in time for the orthodontist.

Further details of the invention are defined in the features of the claims.

DEFINITIONS

As used herein:
"Mesial" means in a direction toward the center of the patient's curved dental arch.
"Distal" means in a direction away from the center of the patient's curved dental arch.
"Occlusal" means in a direction toward the outer tips of the patient's teeth.
"Gingival" means in a direction toward the patient's gums or gingiva.
"Facial" means in a direction toward the patient's lips or cheeks.
"Lingual" means in a direction toward the patient's tongue.

DETAILED DESCRIPTION OF THE PREFERRED EMBODIMENTS

A method of determining the position of orthodontic appliances according to one embodiment of the invention includes the act of obtaining a digital data file that is representative of the shapes of teeth of a dental arch. The data file may be obtained, for example, through the use of a scanning device such as an intra-oral camera that is held in the patient's oral cavity or by the use of X-ray apparatus or other type of radiation apparatus. Alternatively, the digital data file may be obtained through use of a contact probe that engages the surfaces of the patient's teeth at a multitude of locations.

As another alternative, the digital data file representative of the shapes of teeth of the dental arch may be obtained by first taking an impression of the patient's teeth using a curable impression material. Next, a data file is obtained by scanning the impression with a camera or other device or by scanning a physical model that is made from the impression. As yet another option, the data file may be obtained by the use of a mechanical profilometer that mechanically probes the model or by the use of the apparatus described in WO97/03622.

Figure 1:
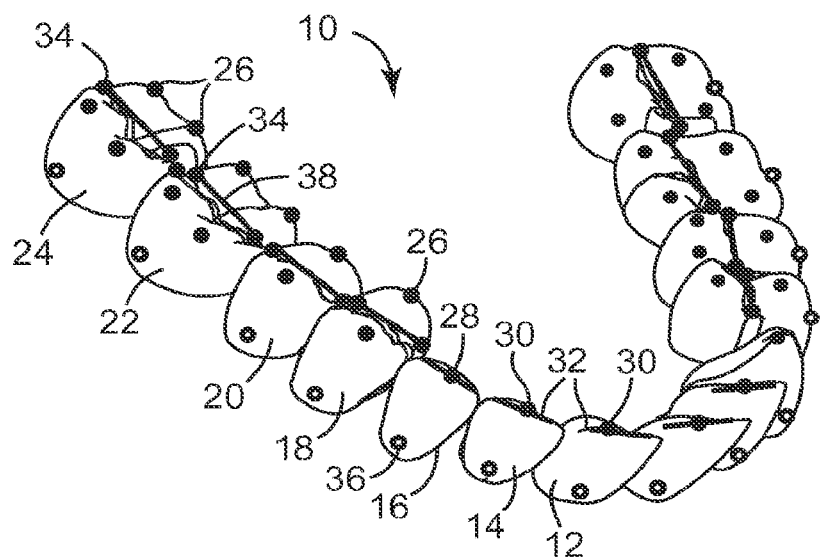
FIG. 1 is a perspective view of a digital image of a dental patient's lower dental arch, illustrating among other things certain landmarks associated with each tooth of the arch.

FIG. 1 is a view of an exemplary dental arch 10 of an orthodontic patient, as might be shown on a display of a computer using a digital data file that is obtained by scanning the dental arch, a model of the arch or an impression of the arch. The virtual dental arch 10 includes a pair of central incisor teeth 12, a pair of lateral incisor teeth 14, a pair of canine or cuspid teeth 16, a pair of first bicuspid or premolar teeth 18, a pair of second bicuspid or premolar teeth 20, a pair of first molar teeth 22 and a pair of second molar teeth 24.

A software program is utilized to analyze the digital data file of the dental arch and segregate the data in the file into separate objects or sub-files representing each individual tooth of the arch. Each object or sub-file is tagged with an identifier representing the tooth type, such as a lower right first molar or an upper right canine. The teeth may be identified by input from a technician. For example, a program may be provided that enables the technician to position a cursor over the image of the maloccluded teeth on a computer monitor and then select or input the appropriate tooth identity. Alternatively, the software can assign an identity to each tooth in sequential order along the dental arches after the technician has verified that all of the expected teeth are present in the image.

Preferably, the software also analyzes the data to remove or modify any erroneous data points and also to add data as needed by estimation. For example, a data file representing a tooth surface that includes a data point significantly outside the normal expected geometrical relationship of adjacent data points could be fixed by data-handling software to remove the erroneous data point. In addition, tooth data points that are missing could be added by such software to create realistic, smoothly curved tooth shapes. Examples of a suitable software program for separating the dental arch data file into sub-files representing individual teeth include "Piano" from Geomagic, Inc. of Durham, N.C. and "InVivoDental", from Anatomage, Inc. of San Jose, Calif. An example of a suitable software program for removing or modifying erroneous data points and adding data as needed in order to smooth contoured surfaces is "Sparkle", also from Geomagic, Inc.

Each tooth sub-file is then analyzed to determine certain structural features or landmarks of the corresponding tooth. For the molar and bicuspid teeth, the location of the tip of each cusp is identified. Examples of these cusp tips are designated by the numeral 26 in FIGS. 1 and 2. The outermost tip of each canine tooth 16 is also identified and is designated by the numeral 28 in FIG. 1. The center of the incisal edge of each lateral tooth 14 and central tooth 12 is also identified, as designated by the numeral 30 in FIG. 1. In addition, an incisal edge line 32 is established for each lateral tooth 14 and central tooth 12.

Figure 2:
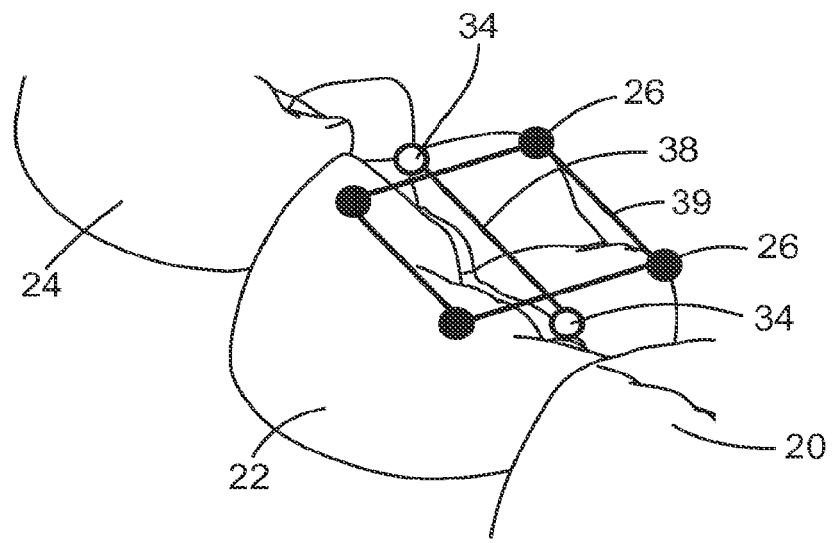
FIG. 2 is an enlarged perspective illustration of a portion of the view shown in FIG. 1.

The marginal ridge saddle points are also identified and are designated by the numeral 34 in FIGS. 1 and 2. Typically, the marginal ridge saddle points 34 are located next to the mesial and distal sides of each molar and premolar tooth 18-24 at the bottom of the recess between opposing facial and lingual cusps, or at a location in the recess that is closest to the gingiva. In addition, a line representing a marginal ridge 38 for each of the molar and premolar teeth 18-24 is defined by establishing a straight line between the marginal ridge saddle points 34 of the respective tooth.

The center of the gingival margin for each tooth 12-24 is also identified and is designated by the numeral 36. For purposes of the present invention, the center 36 of the gingival margin can be determined by viewing the facial surface of the tooth in a lingual direction, and then visually selecting the center of the gingival margin in a mesial-distal direction. The center 36 of the gingival margin is often, but not always, at the location that is the greatest distance from the occlusal edge or occlusal plane of the tooth.

The points representing the molar and premolar cusp tips 26, the outermost tip 28 of the canine teeth 16, the center 30 of the incisal edges and the marginal ridge saddle points 34 may be selected by a technician using, for example, a computing device that displays the image of each tooth. An input device such as a mouse, joystick or keyboard may be used to select the various landmark points. To determine the marginal ridge 38, the software may enable the technician using a mouse to click on a location to establish one saddle point 34 and, while depressing the mouse button, draw a line by moving the curser with the mouse to a second location in order to establish the second saddle point. The mouse button is then released to fix the line in place.

In order to confirm whether or not the selected virtual marginal ridge 38 is properly identified, the software can render invisible any portions of the marginal ridge 38 that extend though the tooth surface. For example, if the selected saddle points 34 are in locations along the sides of the tooth that are too close to the location of the gingiva, a substantial portion of the marginal ridge 38 will be missing from the view on the display as observed by the technician. The technician can then select new saddle points 34 that are located a greater distance from the gingiva to establish a satisfactory virtual marginal ridge 38.

Optionally, a software program may be utilized to at least partially automate the selection of the landmarks. For example, for the sub-files representing the canine teeth, the software may designate the occlusal-most data point as the outermost tip 28. As another example, the software may select the location of the center 30 of the incisal edge by determining the center of the incisal edge line 32 that was previously established by the technician. Preferably, the technician would review the location of landmarks determined by automated landmark selection software and adjust the locations of the landmarks as needed.

Preferably, certain other structural reference aspects are also determined. For instance, an occlusal reference plane 39 may be defined for the molar teeth 22, 24 and the premolar teeth 18, 20, and is shown for exemplary purposes in FIG. 2 for the first molar tooth 22. The occlusal reference plane 39 for each molar tooth 22, 24 may be established, for example, by software using methods of linear regression to determine a reference plane that best fits the four cusp tips 26.

For the premolar teeth 18, 20, the occlusal reference plane 39 may be established by defining a plane that extends through the tip 26 of the facial cusp and is perpendicular to the long axis of the tooth. For the anterior teeth (i.e., the central incisor teeth 12, the lateral incisor teeth 14 and the canine teeth 16), the occlusal reference plane 39 can be established by defining a plane that extends through the center 30 of the incisal edge and is perpendicular to the long axis of the tooth. The long axis of the teeth 12-20 may be visually estimated and identified by the technician by referring to a display of the tooth image, or established using the methods described in U.S. Pat. No. 7,033,327 (Raby) entitled "Method of Determining the Long Axis of an Object".

Next, a coordinate system is established for each tooth 12-24 of the dental arch 10. The origin of the coordinate system may be placed at any convenient location. One possible location for the origin of the coordinate system is a point along the occlusal plane or along the marginal ridge, such as a location where such plane or ridge intersects the mid-sagittal plane of the tooth. Another possible location for the origin of the coordinate system is a location on the facial surface of the tooth, such as the central location known as the facial axis point 41 ("FA Point") that will be described below with reference to FIG. 3.

Figure 3:
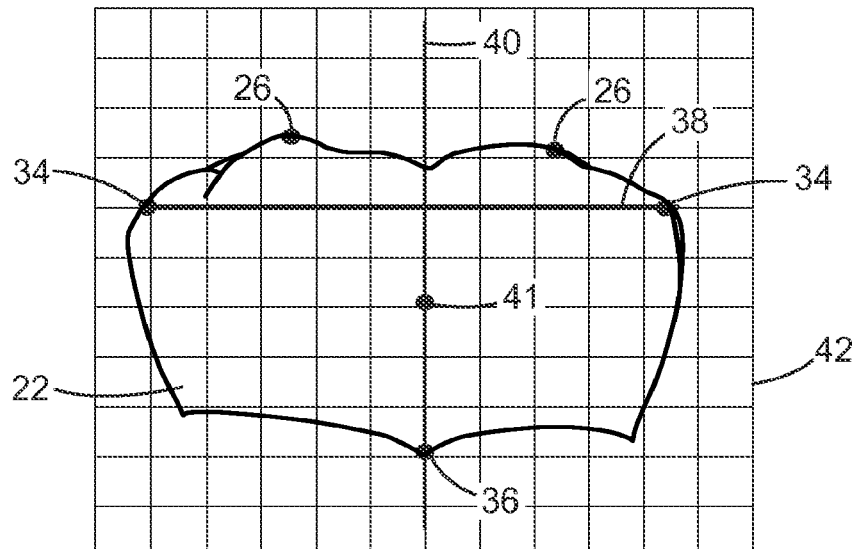
FIG. 3 is a front elevational view looking in a lingual direction of the lower right first molar tooth of the dental arch shown in FIG. 1, additionally depicting certain landmarks associated with the tooth along with an optional viewing grid.

To determine the location of the FA Point 41, a mid-sagittal reference plane 40 for the tooth is first defined. For purposes of explanation, the edge of the mid-sagittal plane 40 is depicted in FIG. 3 for the first molar tooth 22. The orientation of the reference plane 40 may be determined by a technician, using a display and an input device. As another option, the mid-sagittal reference plane 40 may be established by software using, for example, the methods described in published U.S. Patent Application No. 2007/0238064 (Stark et al.) entitled "Automatic Adjustment of an Orthodontic Bracket to a Desired Mesio-Distal Position within a Three-Dimensional (3D) Environment".

Next, the Facial Axis of the Clinical Crown ("FACC") is defined by identifying the curved line segment formed by the intersection of the mid-sagittal plane and the facial surface of the tooth. The FA Point 41 is then defined as the point that is equidistant from the occlusal edge or occlusal-most point on the FACC and the gingival margin of the crown. The coordinate system is then oriented and fixed in place such that (a) the origin of the coordinate system coincides with the FA Point, (b) the horizontal or mesial-distal coordinate axis extends in a direction perpendicular to the mid-sagittal plane and (c) the vertical or occlusal-gingival coordinate axis extends in a direction perpendicular to the occlusal plane of the respective tooth.

Preferably, the tooth coordinate system is reviewed before proceeding further in order to ensure that the coordinate system is properly oriented with respect to each tooth of the dental arch 10. This step is often considered desirable, as the shape of the patient's teeth may deviate from an average shape. Moreover, the teeth may include abnormal features such as worn or missing portions that may have been overlooked or not detected by the software. Optionally, and as shown in FIG. 3, a visual grid 42 that is aligned with the selected coordinate system can be presented on the display device while a technician makes a visual check of the origin and any adjustments in the position of the origin as may be desired. In this view, the technician can also check and adjust the torque angle of the tooth 22 as desired.

If the tooth image shows that portions of the tooth are missing or that excessive wear has occurred, the technician may elect to replace the missing or worn portions by estimating the original shape of the tooth. For example, data representing the missing or worn portions may be manually drawn by the technician using an input device such as a mouse or joystick. Alternatively, the computer may have a library of tooth data files representing models of average teeth and in that case the technician can use all or a portion of those files to replace the data representing the missing or worn portions. As another alternative, and for worn or missing cusps, the technician may elect to simply adjust the position of the point representing the cusp tip (such as cusp tip 26) and omit steps that could be otherwise taken to apply new surface contours to the tooth. Another option is to use the first-defined cusp tips to define an occlusal plane, and then allow the technician to manually adjust the plane by means of clicking- and dragging on boundary features of the plane, by editing numerical plane parameters directly or via interactive GUI controls, or by other means.

Figure 4:
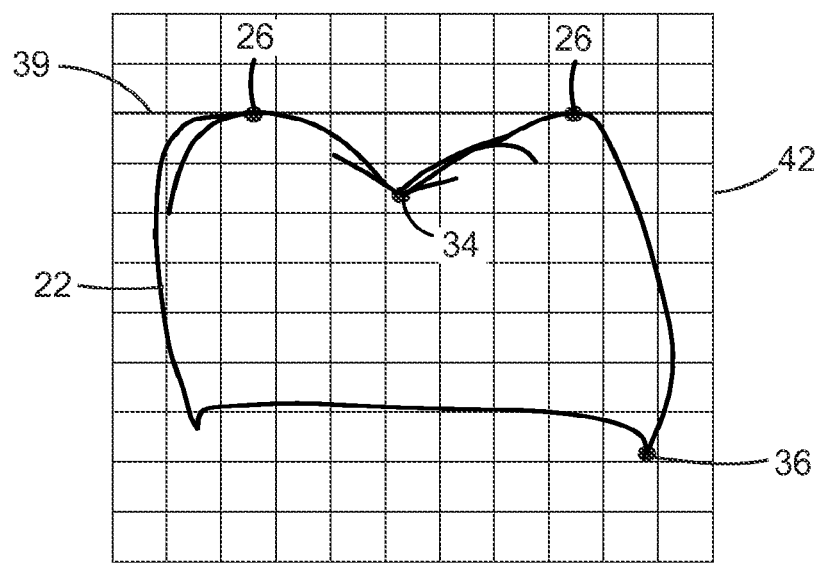
FIG. 4 is a side elevational view of the lower right first molar tooth shown in FIG. 3, except looking at the tooth in a mesial direction.

FIG. 4 is a view of the first molar tooth 22 shown in FIG. 3 but looking in a mesial direction. Also shown in FIG. 4 is an optional viewing grid 42 as may be provided on the display device. In this view, the technician can check and make any necessary adjustments on the location of the points initially selected for the cusp tips 26 and the center 36 of the gingival margin. Additionally, in this view the technician can check and make any desired adjustments in the angle of the long axis of the tooth 22 in order to ensure that the coordinate system is properly oriented with a displayed view of the occlusal plane of the tooth 22. A similar check of the various landmarks and the coordinate systems can be carried out for the second molar tooth 24 as well as for the premolar teeth 18, 20.

Figure 5:
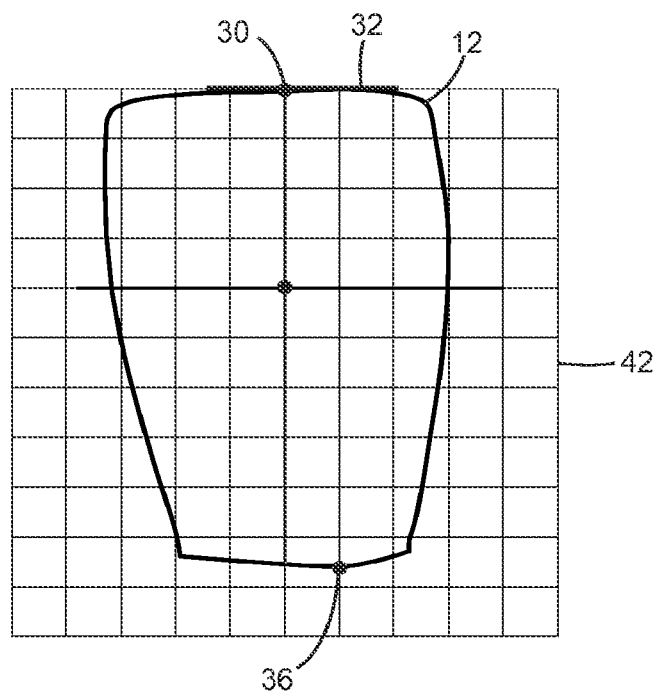
FIG. 5 is a side elevational view somewhat similar to FIG. 3 except that the tooth is the lower right central incisor tooth of the dental arch shown in FIG. 1.

FIG. 5 is a facial view of one of the central incisor teeth 12 along with an optional reference viewing grid and a coordinate system that has been established for the tooth 12. In this view, the technician may review and revise if needed the angle of the tooth 12 relative to the coordinate system in order to ensure that the coordinate system is properly aligned with the line 32 representing the incisal edge. In this view, the technician may also review and revise, if necessary, the location of the center 30 of the incisal edge and the center 36 of the gingival margin.

Figure 6:
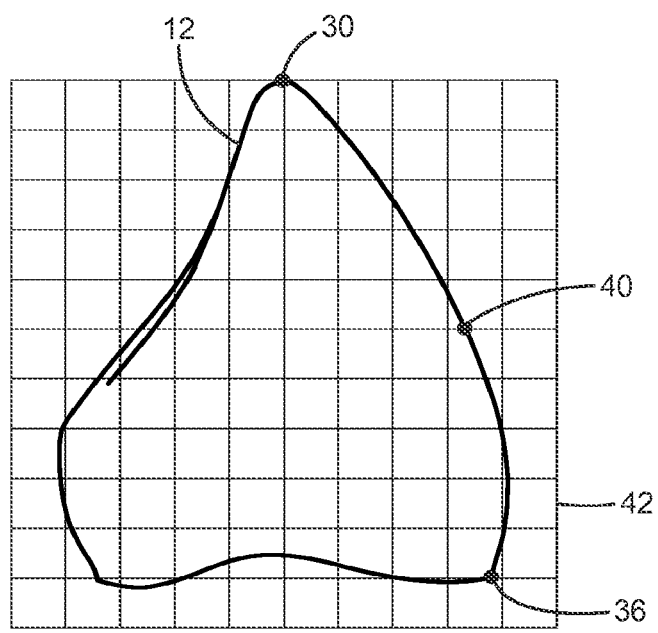
FIG. 6 is a side elevational view of the lower right central incisor tooth shown in FIG. 5, except looking at the tooth in a mesial direction.

FIG. 6 is a distal view of the central incisor tooth 12 shown in FIG. 5 along with the tooth's coordinate system and the optional grid, as may be observed on the display associated with the computer. In this view, the technician may check and make any necessary adjustments in the location of the origin of the coordinate system. In addition, in this view the technician may review and make any necessary adjustments in the torque angle of the tooth 12 relative to its coordinate system.

Figure 7:
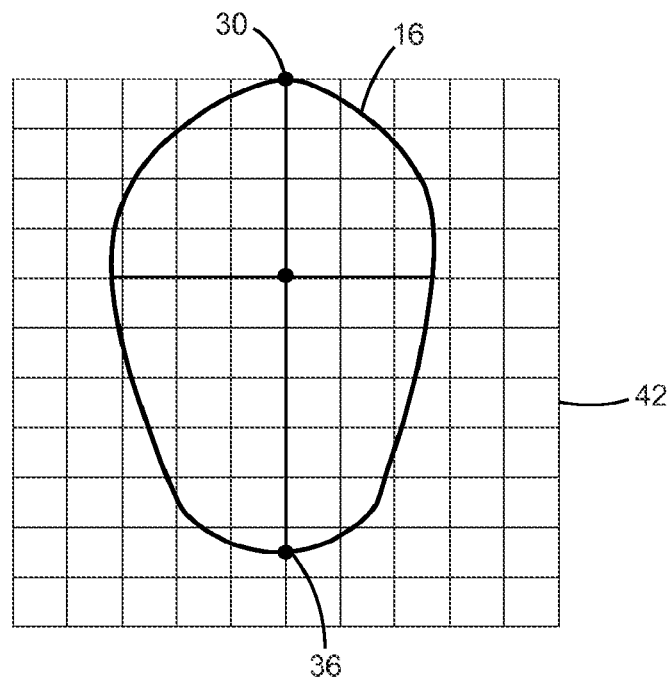
FIG. 7 is a side elevational view somewhat similar to FIG. 3 except that the tooth is the lower right canine tooth of the dental arch shown in FIG. 1.

FIG. 7 is an illustration of one of the canine teeth 16 as it might appear on the computer display, looking toward the tooth 16 in a lingual direction. In this view, the technician may check and adjust as needed the position of the origin of the tooth's coordinate system, optionally using a viewing grid. The technician may also check and revise as needed the location of the previously selected point representing the outermost tip 28 and the point representing the center 36 of the gingival margin, as well as the alignment of the coordinate system with the tooth's long axis.

Figure 8:
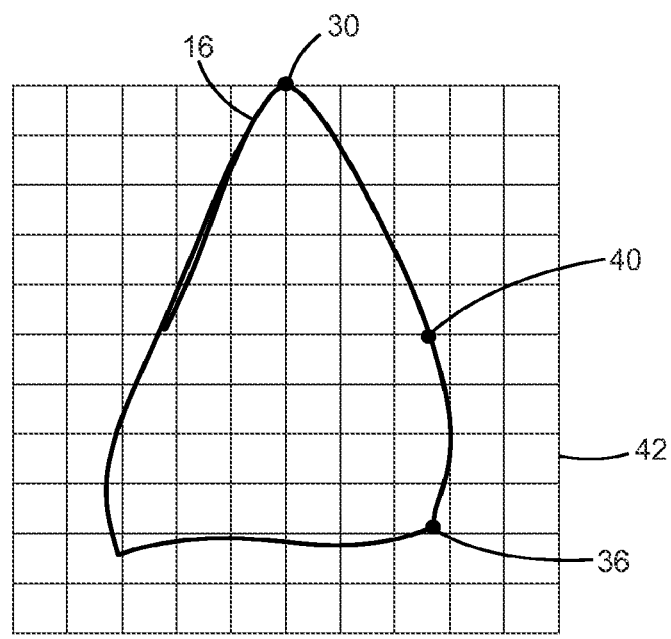
FIG. 8 is a side elevational view of the lower right canine tooth shown in FIG. 7, except looking at the tooth in a mesial direction.

FIG. 8 is another view of the canine tooth 16 shown in FIG. 7 as it might appear on the computer display with the optional viewing grid, looking toward the tooth in a distal direction. Using the view depicted in FIG. 8, the technician may check and adjust the previously selected origin of the tooth's coordinate system. The technician may also review and adjust as needed the torque angle of the tooth 16 relative to the coordinate system.

After the technician is satisfied that each coordinate system is properly oriented with respect to its respective tooth 12-24, a set of virtual orthodontic appliances are placed on the virtual teeth 12-24 in initial positions, using the coordinate systems to define relative positions between the appliances and the teeth 12-24. A variety of methods are available for selecting the initial locations of the appliances. For example, the practitioner may elect to place various appliances on the teeth at certain pre-selected heights that the practitioner has used in the past and/or have been recommended by other practitioners. Alternatively, the practitioner may choose placement heights for the appliances that are identical or similar to placement heights suggested by the manufacturer.

Table I is an exemplary positioning chart for certain orthodontic appliances according to the teachings of Dr. Anoop Sondhi. The values for the heights in Table I are measured from the occlusal plane of the tooth to a central location in the archwire slot of the corresponding appliance. Other heights or measuring techniques may be used as well, and may be especially desirable with other types of appliances. The practitioner may also elect to deviate from any of these heights in accordance, for example, with the particular shapes of the teeth and/or with the particular malocclusion at hand.

TABLE I

Initial Appliance Placement Heights

| MAXILLARY | HEIGHT |
| --- | --- |
| Central Incisors | 4.0 mm |
| Lateral Incisors | 4.0 mm |
| Canines | 4.5 mm |
| First Premolars | 4.5 mm |
| Second Premolars | 4.5 mm |
| First Molars | 3.5 mm |
| Second Molars | 3.5 mm |

| MANDIBULAR | HEIGHT |
| --- | --- |
| Central Incisors | 3.5 mm |
| Lateral Incisors | 3.5 mm |
| Canines | 4.0 mm |
| First Premolars | 4.0 mm |
| Second Premolars | 4.0 mm |
| First Molars | 3.5 mm |
| Second Molars | 3.5 mm |

Figure 9:
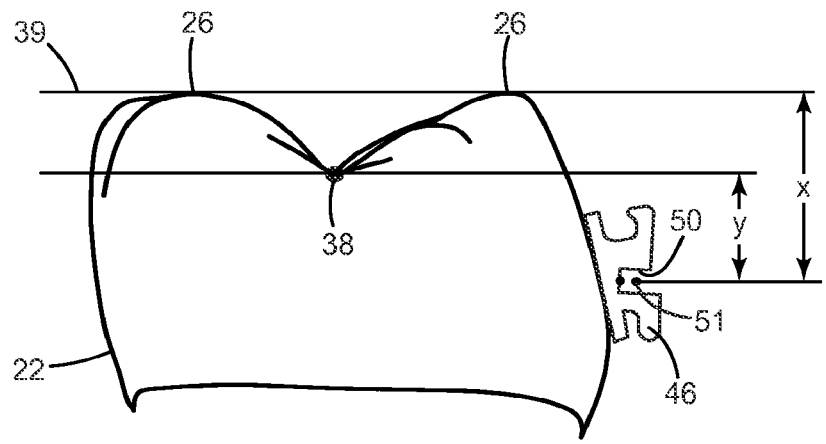
FIG. 9 is a side elevational view of the lower right first molar tooth somewhat similar to the view depicted in FIG. 4 and looking at the tooth in a mesial direction, additionally illustrating an orthodontic appliance that has been placed on the facial surface of the tooth.

FIG. 9 is an illustration of an exemplary virtual appliance 46 that has been placed on the virtual first molar tooth 22. Using software, the appliance 46 is placed at the height identified in Table I, which in this instance is 3.5 mm from the molar occlusal plane 39. The direction of measurement for the appliance height in FIG. 9 is in a direction perpendicular to the molar occlusal plane and in this example is determined from a point 51 that is located 0.0125 inch (0.32 mm) in a facial direction from mesial-distal and occlusal-gingival center of the bottom or lingual side of an archwire slot 50 of the appliance 46. In FIG. 9, the letter "x" represents the initial, preselected height of 3.5 mm. The dimension "0.0125 inch (0.32 mm)" is used in this example since it represents one-half of the horizontal width of the rectangular-shaped archwire that is often used during the final stages of orthodontic treatment, and consequently represents the center of the expected archwire when viewed in a reference plane perpendicular to its longitudinal axis.

The virtual appliance 46 is seated against the facial surface of the tooth 22, preferably with a small dimensional allowance to account for the thickness of a bonding adhesive. If the contour of the tooth-facing base surface of the of the appliance 46 does not exactly match the contour of the section of the tooth surface that is intended to receive the appliance 46, the orientation of the appliance 46 is adjusted as needed to an orientation that represents a best-fit relationship. As one option, the methods described in U.S. Pat. No. 7,210,929 (Raby et al.) entitled "Method of Orienting an Orthodontic Appliance to a Tooth" may be utilized by software to seat the base of the appliance 46 against the tooth surface. However, the initial height of the appliance 46 when seated against the tooth surface is equal to the initial placement height of 3.5 mm.

As can be appreciated by reference to FIG. 9, the appliance height as suggested by the pre-selected prescription may result in placing the appliance on a section of the facial tooth surface that is not parallel to the long axis of the tooth, which may cause the archwire slot of the appliance to have an orientation that is not parallel with the occlusal reference plane of the tooth if the archwire slot was perpendicular to the base of the appliance. For this reason, and in accordance with the straight wire concept mentioned above, appliances such as appliance 46 often have a tooth-facing base surface that is oriented at an angle which is intended to match the angle of the tooth surface at the location where the appliance is intended to be bonded to the tooth, while retaining the archwire slot in a horizontal orientation. In particular, in such appliances the angle of the tooth-facing base surface is oriented such that a reference axis extending perpendicular to a reference plane tangent to the base surface at the center of the base extends at a non-parallel angle relative to the horizontal (i.e., occlusal and gingival) walls of the archwire slot 50. This angle, often termed the "torque angle", was determined by Dr. Lawrence Andrews to represent an average ideal angle of the corresponding tooth after a study of a number of model dental arches that were considered to represent ideal occlusions. Table II sets out the ideal torque values as determined by Dr. Andrews, which are often used by manufacturers for selecting the angle of the tooth-facing base surface of orthodontic appliances.

TABLE II

| Torque Values | |
|---|---|
| MAXILLARY | TORQUE |
| Central Incisors | +7° |
| Lateral Incisors | +3° |
| Canines | −7° |
| First Premolars | −7° |
| Second Premolars | −7° |
| First Molars | −9° |
| Second Molars | −9° |
| MANDIBULAR | TORQUE |
| Central Incisors | −1° |
| Lateral Incisors | −1° |
| Canines | −11° |
| First Premolars | −17° |
| Second Premolars | −22° |
| First Molars | −30° |
| Second Molars | −35° |

Figure 10:
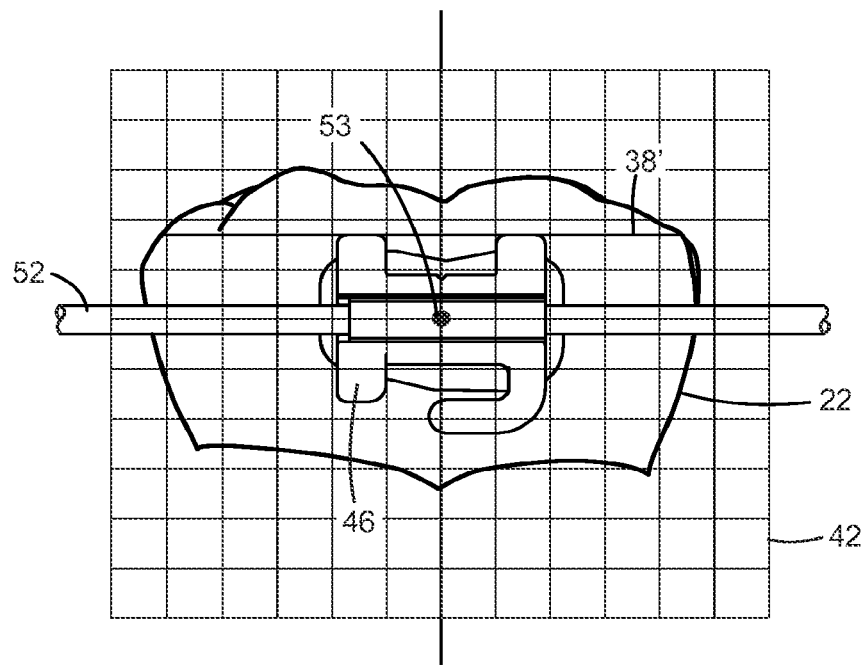
FIG. 10 is a side elevational view similar to FIG. 9, except looking at the tooth and the appliance in a lingual direction.

The technician may use the view shown in FIG. 9 in order to visually confirm that the contour of the base surface of the appliance 46 sufficiently matches the contour of the adjacent tooth surface. The tooth 22 and the appliance 46 may also be viewed on the display as shown in FIG. 10 along with the optional grid 42, looking in a lingual direction parallel to the occlusal plane 39. Optionally, and as illustrated, a virtual archwire 52 may be seated in the archwire slot 50 in order to enhance the technician's view of the alignment of the archwire slot 50. In addition, a line 38' representing the height of the marginal ridge 38 of the tooth 22 is also shown in the display device.

If the torque of the appliance 46 does not provide a satisfactory fit to the surface of the tooth 22, the technician may elect to select an appliance with a different torque value and/or changing the position of the appliance 46 on the tooth (which, however, could compromise the prescribed appliance height or other placement guidelines, such as mesial-distal position or even tip). Another option is to accept a compromise of the fit between the appliance 46 to the teeth, with the intent of later filling the wedge-shaped space between the appliance base and facial surface of the tooth by an adhesive that is cured to form a custom bracket base.

The orientation of the appliance 46 is then inspected to ensure that the angulation of the appliance in directions about a facial-lingual reference axis is satisfactory. To this end, the virtual appliance 46 may be rotated about the facial-lingual reference axis (designated 53 in FIG. 10) as needed to ensure that the longitudinal axis of the archwire slot 50 is parallel to the line 38' representing the marginal ridge.

Once the technician is satisfied that the appliance 46 is properly aligned with the marginal ridge line 38', the distance between the archwire slot 50 and the marginal ridge line 38 is determined by software. This distance is measured along a reference axis perpendicular to the occlusal plane of the tooth 22 along the mid-sagittal plane of the tooth 22 and is represented by the letter "y" in FIG. 9.

Based on the distance y, the software program then suggests new appliance heights for the first and second premolar teeth 18, 20 and the second molar tooth 24 based on the distance y determined in connection with the first molar tooth 22. The new appliance heights for the teeth 18, 20, 24 are provided in terms of the distance between the marginal ridges and the archwire slots of the corresponding appliances. As presently preferred, the distance between the archwire slot and the marginal ridges for the appliances and the corresponding teeth 18, 20 and 24 is set to be the same or approximately the same as the distance y that was determined for the first molar tooth 22. As a result, the marginal ridges of the teeth 18-24 will be in proper, level alignment at the conclusion of treatment when the archwire extends in a level, flat plane.

The technician also views each tooth 18, 22, 24 with the corresponding appliance in a lingual direction and adjusts the angulation of each appliance as needed in order to align the appliance with the marginal ridge line, similar to the adjustment of the angulation described in connection with the appliance 46. The technician also makes any necessary adjustment in the appliance positions to compensate for possible interference with other teeth or to compensate for interference between two teeth when in final occlusion. For example, upper second molar teeth often interfere with opposing lower molar teeth. Consequently, it may be desirable to move the appliances for the upper second molar teeth toward the occlusal plane while keeping the archwire slot parallel with the marginal ridge in order to reduce the risk of such interference.

The software then determines the difference, or "Δ", between the new suggested appliance height for the first premolar tooth 18 and the initial pre-selected height as set out in Table II. To this end, the software calculates the distance between the mesial-distal and occlusal-gingival center of the bottom or lingual side of the archwire slot of the appliance to the occlusal plane of the tooth 18, measured in a direction perpendicular to the occlusal plane. This revised appliance height is then compared to the value in Table II for the first premolar tooth (in this instance, 4.0 mm) and the difference Δ is then noted.

Figure 11:
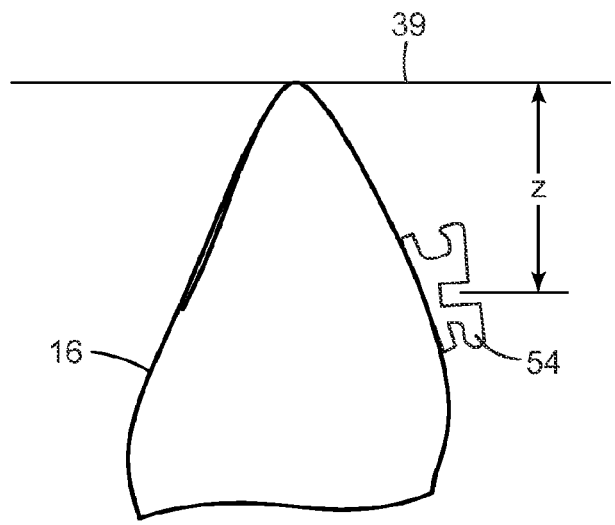
FIG. 11 is a side elevational view, looking in a mesial direction, of the lower right first premolar tooth of the dental arch shown in FIG. 1 along with an orthodontic appliance that has been placed on the facial surface of the tooth.

Next, the software determines suggested revised heights for the appliances of the remaining teeth, namely the central incisors 12, lateral incisors 14 and canines 16. For exemplary purposes, the canine tooth 16 is illustrated in FIG. 11 looking in a mesial direction. Additionally, a virtual canine appliance 54 has been placed on the surface of the canine tooth 16. In this instance, the appliance 54 is positioned on the tooth 16 at a distance that is designated "z" in FIG. 11 from the height of the tooth's occlusal plane 39. The distance z in this example is determined by adjusting the initially pre-selected height such as set out in Table II (i.e., 4.0 mm) by the difference, or Δ, that was determined for the first premolar tooth. For example, if the difference, or Δ, calculated for the first premolar tooth 18 was 0.3 mm, the new suggested height z of the appliance 54 in FIG. 11 relative to the occlusal plane is 4.3 mm.

Subsequently, the technician may view the canine tooth 16 from its facial side, looking in a lingual direction, in order to review the angulation of the appliance 54. For example, the technician may desire to align the sides of the appliance 54 or viewings of the appliance 54 to be parallel with the long axis of the tooth 16. As an additional option, the software may display the long axis of the tooth 16 using a method similar to the methods described in U.S. Pat. No. 7,033,327 (Raby).

Virtual appliances are also placed on the central incisor teeth 12 and the lateral incisor teeth 14 in a method similar to the method described in connection with the canine tooth 16. However, it may be desirable to place appliances for the central and lateral teeth in positions closer to the corresponding incisal edges in comparison to appliances for the canine teeth in order to achieve more satisfactory final tooth positions at the conclusion of treatment. Accordingly, the software may use preselected rules for determining the appliance heights for the central and lateral teeth relative to the appliance heights for the canine teeth. For example, the difference, or Δ, that was used to determine new appliance heights for the canine teeth 16 can be decreased by 0.5 mm for the central and lateral appliances so that such appliances are placed 0.5 mm nearer to the corresponding tooth's occlusal plane. In this regard, the appliance heights for the central incisor teeth 12, the lateral incisor teeth 14 and the canine teeth 16 is established with reference to the tooth's occlusal plane since these teeth lack marginal ridges.

Once the appliances have been initially positioned on the virtual teeth 12, 14, the technician may review the placement from a facial view looking in a lingual direction. If the teeth 12, 14 have a well-defined incisal edge, the technician may elect to adjust the angulation of the appliance as needed in order to align the longitudinal axis of the appliances with the incisal edge line 32 of each tooth respectively. Alternatively, and also as an option in instances where the incisal edge is not well-defined, the longitudinal axis of the appliance (optionally made visible by a scribe line) is aligned with the longitudinal axis of the tooth.

Optionally, the steps set out above are first carried out for the lower arch and then carried out for the upper arch. For each arch, the steps could be carried out for both quadrants simultaneously and the results could be averaged so that the appliance height for each tooth is identical to the same tooth in the opposite quadrant. However, in some cases it may be preferable to avoid using averaged results, such as in instances where the shapes of the same teeth in opposite quadrants are significantly different.

Optionally, the software could enable the technician or orthodontist to see the virtual teeth moved to desired finished positions based upon the suggested placement of the appliances and the effect to the marginal ridge alignment when the appliances are allowed to move along a straight archwire. Preferably, the technician or orthodontist could observe the teeth in at least four views: initial orientations without appliances, initial orientations with appliances, final orientations with appliances and final orientations without appliances. After viewing one or more of those images, the technician or orthodontist may elect to change the suggested position of one or more appliances in order to achieve a desired effect for the particular patient.

As an additional option, the software may enable the orthodontist or technician to replace one or more of the appliances with another appliance having a different prescription value (such as torque or in/out) in order to visualize the effect of different prescriptions on the marginal ridges when the appliances and teeth are moved along a straight archwire. As a further option, the effect of the original appliance and the new appliance may be visually compared in overlaid, contrasting fashions by the method set out in U.S. Pat. No. 6,733,289 (Manemann et al.) entitled "Method and Apparatus for Selecting a Prescription for an Orthodontic Brace".

A number of alternative methods are possible. For example, instead of using a preselected table of appliance heights determined from the cusps of the teeth such as shown in Table I, the practitioner may elect to select an appliance height for the first molar tooth 22 relative to the marginal ridge 38. The software can then determine suggested appliance positions for the remaining posterior teeth based on alignment of the marginal ridges, and for the anterior teeth based on a preselected relationship between the anterior appliances and the posterior appliances. As yet another option, the software could initially place the appliance 46 on the first molar tooth 22 at a location in the geometric center of the facial surface of the tooth 22 or the FA Point of the tooth 22. From this initial position, the software can then calculate the height of the appliance 46 from the marginal ridge 38 in order to determine suggested positions for the remaining appliances. As additional options, the practitioner may elect to provide a selected appliance height relative to the marginal ridge for a posterior tooth other than the first molar tooth 22, or elect to prompt the software to determine the FA point and virtually place the first appliance on a posterior tooth other than the first molar tooth 22. However, use of the first molar tooth 22 as the first tooth for determining appliance position may be preferred by many practitioners since the first molar tooth 22 is often considered as an "anchor" tooth for purposes of moving teeth. Moreover, the first molar teeth 22 are normally present in the occlusion of patients seeking orthodontic treatment, in comparison to other teeth that may be missing or not fully erupted.

Preferably, the software also uses the digital data file to calculate the distance between the suggested height of each appliance and the corresponding occlusal plane. Those distances can then be provided to practitioner in case rebonding of an appliance is necessary during the course of treatment. These distances can also be used if desired to construct a jig or other placement apparatus for facilitating positioning of the appliance during a rebonding procedure.

As an additional alternative, the present invention can be incorporated into a graphical user interface ("GUI") tool in treatment planning, appliance inventory and/or appliance ordering software. In such software, the practitioner could enter his or her preferences for appliances, appliance heights and other information so that use of the software is facilitated.

The present invention is especially useful during the manufacture of indirect bonding apparatus such as transfer trays and jigs since the determined positions can be used to ensure proper placement of the appliances in the bonding apparatus. The practitioner may prefer, for example, to provide placement information to the manufacturer in terms of measurements from the cusps, occlusal plane or incisal edge of the various teeth. Using the principles of the present invention, the manufacturer or practitioner can then utilize the practitioner's placement information in order to check for proper marginal ridge alignment and suggest revised placement information as desired.

Preferably, the revised placement information is provided to the practitioner in the form of a set of appliance heights that utilize the cusps, incisal edge and/or occlusal plane as a point of reference in placing the appliances. Such practice aids the practitioner in instances when an appliance has spontaneously and unintentionally debonded from the patient's tooth during the course of treatment. In those instances, the practitioner can use a conventional height gauge for placing the appliances during a rebonding procedure without the need to locate the marginal ridge and attempt the difficult procedure of positioning the appliance at a certain distance from the marginal ridge.

The present invention is also useful for practitioners that use a direct bonding technique in which the appliances are positioned on the surfaces of the teeth with a height gauge that uses the cusps or incisal edge as a point of reference. Because the software provides the revised placement information in terms of distances from the cusps, incisal edges or occlusal planes, a conventional height gauge can be used to place and bond the appliances to the teeth.

Figure 12:
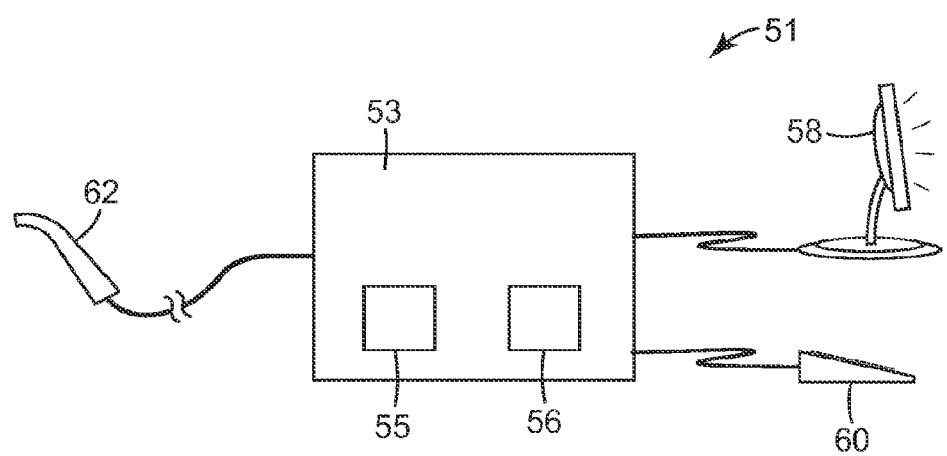
FIG. 12 is a block diagram illustrating an exemplary system for carrying out the appliance positioning methods of the present invention.

FIG. 12 is a block diagram of an exemplary system 51 that can be used to carry out the methods of the present invention. The system 51 includes a computer 53 having memory 55 for storing digital data files. The computer 53 includes software programs 56 for analyzing the data files and carrying out the steps mentioned above for determining the position of orthodontic appliances. A display 58 is operatively connected to the computer 53 for providing various images including the views of the teeth as represented in FIGS. 1-11. An input device 60 such as a mouse and keyboard is also connected to the computer 53 for manipulating the images and for inputting various commands.

The system 51 further includes a scanning device 62 such as the Lava brand chairside intra-oral scanner from Brontes Technologies, Inc. of Lexington, Mass. Optionally, the scanning device 62 is located in the practitioner's office and is operatively connected via the internet to the computer 53, which is remotely located in a manufacturing facility for making indirect bonding apparatus. Preferably, however, the practitioner's office also includes a computer terminal so that the practitioner can review the various suggested appliance positions, observe predicted final tooth positions and make any revisions as are desired.

All of the patents and patent applications mentioned above are hereby expressly incorporated by reference into the present disclosure. Moreover, a number of alternatives are also possible. As such, the present invention should not be deemed limited to the description of the currently preferred embodiments set out above, but instead only by a fair scope of the claims that follow.

What is claimed is:

1. A method for determining the position of orthodontic appliances in a bonding guide, the method comprising:

obtaining a digital data file representative of the shapes of teeth of a dental arch;

displaying a digital representation of the dental arch from the data file, the representation including a first tooth of the dental arch, and a second tooth of the dental arch, and a third tooth of the dental arch;

using the digital data file to determine marginal ridge heights of the first tooth, second tooth, and third tooth;

selecting an appliance height for the first tooth from a preexisting prescription for a plurality of teeth of the dental arch including the first, second, and third teeth, wherein the prescription includes a prescribed appliance height of each tooth of the plurality of teeth based on a prescribed distance from the occlusal plane height of each tooth;

positioning a digital representation of an appliance on the digital representation of the first tooth at the prescribed height;

determining the distance between the prescribed appliance height for the first tooth and the marginal ridge height of the first tooth, the distance being determined only after appliance height is selected;

positioning a digital representation of an appliance on the digital representation of the second tooth at the prescribed height for the second tooth;

modifying the appliance height on the digital representation for the second tooth to a distance from the marginal ridge height of the second tooth that is based at least in part on the determined distance between the selected appliance height for the first tooth and the marginal ridge height of the first tooth;

determining the distance either between the marginal ridge height of the first tooth and the occlusal plane height of the first tooth or between the marginal ridge height of the second tooth and the occlusal plane height of the second tooth, the distance determined defining a prescription modifier distance;

modifying an appliance height for at least the third tooth based at least in part on the addition of the prescription modifier distance to the prescribed distance for the third tooth; and positioning a digital representation of an appliance on a digital representation of the third tooth at the modified appliance height to create a modified digital representation of the dental arch including positioned first, second, and third appliances; and making an indirect bonding apparatus from the modified digital representation in order to locate the appliances relative to the apparatus according to the positioned heights.

2. A method of determining the position of orthodontic appliances according to claim 1 wherein the proposed appliance height for the second tooth is a distance from the marginal ridge height of the second tooth that is the same as the calculated distance.

3. A method of determining the position of orthodontic appliances according to claim 1 wherein the first tooth is a first molar tooth and wherein the second tooth is a premolar tooth that is in the same quadrant as the first molar tooth.

4. A method of determining the position of orthodontic appliances according to claim 1, wherein determining the prescription modifier distance is carried out for a premolar tooth and wherein modifying an appliance height for the third tooth is carried out for one or more of the central, lateral or canine teeth.

5. A method of determining the position of orthodontic appliances according to claim 1, wherein modifying an appliance height for at least the third tooth is carried out by modifying the determined distance between the appliance height and the occlusal plane height by the prescription modifier distance.

6. A method of determining the position of orthodontic appliances according to claim 1 wherein modifying an appliance height for at least the third tooth is carried out by modifying the determined distance between the appliance height and the occlusal plane height by a preselected amount that varies from the prescription modifier distance.

7. A method of determining the position of orthodontic appliances according to claim 6 wherein the act of defining an occlusal plane is carried out by determining the locations of at least two cusps of the corresponding tooth.

8. A method of determining the position of orthodontic appliances according to claim 1 and including the act of defining an occlusal plane for the molar tooth using the digital data file.

9. A method of determining the position of orthodontic appliances according to claim 1 and including the act of selecting an appliance height for at least one canine, lateral or central incisor tooth by using the appliance height determined for at least one of the molar appliance and the premolar appliance.

10. A method of determining the position of orthodontic appliances according to claim 1, and including the act of selecting an appliance height for at least one canine, lateral or central incisor tooth, wherein the act of selecting an appliance height for at least one canine, lateral or central incisor tooth is carried out by determining the distance between the appliance height for the premolar tooth and the occlusal plane of such premolar tooth.

11. A method of determining the position of orthodontic appliances according to claim 1 wherein the occlusal plane height is determined using digital data representative of the location of one or more missing tooth surfaces.

12. A method for determining the position of orthodontic appliances comprising:

obtaining a digital data file representative of the shapes of teeth of a dental arch;

using the digital data file to determine, via one or more computers, first feature heights of a first tooth of the dental arch, a second tooth of the dental arch, and a third tooth of the dental arch;

selecting an appliance height for the first tooth from a prescription for a plurality of teeth of the dental arch, including the first, second, and third teeth, the prescription including a prescribed appliance height of each tooth of the plurality of teeth based on a prescribed distance from a second feature height;

determining the distance, via one or more computers, between the selected appliance height for the first tooth and the first feature height of the first tooth, the distance being determined after appliance height is selected;

proposing an appliance height for the second tooth, via one or more computers, that is based at least in part on the determined distance between the selected appliance height for the first tooth and the first feature height of the first tooth;

determining the distance, via one or more computers, between the proposed appliance height of the second tooth and the second feature height of the second tooth, the distance so determined defining an offset distance;

calculating the difference, if any, between the offset distance and the prescribed distance for the second tooth of the predefined prescription, the difference calculated via one or more computers and defining a modifier distance;

proposing an appliance height for the third tooth based at least in part on the addition of the modifier distance to the prescribed distance for the third tooth;

positioning a digital appliance on a digital representation of the third tooth at the proposed appliance height to create a digital model of the bracket and third tooth; and displaying the digital model of the appliance and third tooth; and making an indirect bonding apparatus from the digital model of the appliance and third tooth in order to locate the appliance relative to the apparatus according to the proposed height.

13. The method of claim 12, wherein the first feature height is a marginal ridge height, and wherein second feature height is an occlusal plane height.

14. A method of determining the position of orthodontic appliances according to claim 12 wherein determining the modifier distance is carried out for a premolar tooth and wherein proposing an appliance height for the third tooth is carried out for one or more of the central, lateral or canine teeth.

15. A method of determining the position of orthodontic appliances according to claim 12, wherein proposing an appliance height for at least the third tooth is carried out by modifying the determined distance between the appliance height and the second feature height by the prescription modifier distance.

16. A system for positioning orthodontic appliances, the system comprising:

a scanner configured to generate a digital data file representative of the shapes of teeth of a dental arch;

a computing device having a graphical user interface in operative communication with the scanner and including a processor configured to:

access the digital data file;

use the digital data file to determine first feature heights of a first tooth of the dental arch, a second tooth of the dental arch, and a third tooth of the dental arch;

determine an appliance height for the first tooth from a prescription for a plurality of teeth of the dental arch, including the first, second, and third teeth, the prescription including a prescribed appliance height of each tooth of the plurality of teeth based on a prescribed distance from a second feature height on each tooth;

determine the distance between the determined appliance height for the first tooth and the first feature height of the first tooth, the distance defining an offset distance and being determined after the appliance height is determined;

propose an appliance height for the second tooth that is based at least in part on the offset distance;

calculate the difference, if any, between the offset distance and the prescribed distance for the second tooth of the predefined prescription, the difference defining a modifier distance;

propose an appliance height for the third tooth based at least in part on the addition of the modifier distance to the prescribed distance for the third tooth; and place a first digital representation of an appliance on a digital representation of the third tooth at the proposed appliance height to create a digital model of the first appliance and third tooth; and display, via the graphical user interface, the digital model of the first appliance and third tooth.

17. The system of claim 16, wherein the processor is further configured to:
- display, via the graphical user interface, a digital representation of the dental arch, including the first tooth, and the second tooth, and the third tooth;
- place a second digital representation of an appliance on the digital representation of the first tooth at the prescribed height for the first tooth;
- place a third digital representation of an appliance on the digital representation of the second tooth at the prescribed height for the second tooth;
- modify the appliance height on the digital representation for the second tooth to a distance from the first feature height of the second tooth that is based at least in part on the offset distance;
- display, via the graphical user interface, a modified digital representation of the dental arch including placed first, second, and third digital appliances.

18. The system of claim 16, wherein the first feature height is a marginal ridge height, and wherein second feature height is an occlusal plane height.

19. The system of claim 18, wherein the processor is further configured to concurrently display, via the graphical user interface, the modified digital representation and a digital representation of the dental arch without appliances.

* * * * *

UNITED STATES PATENT AND TRADEMARK OFFICE
CERTIFICATE OF CORRECTION

PATENT NO. : 9,503,282 B2  
APPLICATION NO. : 13/063967  
DATED : November 22, 2016  
INVENTOR(S) : Robert Kody Page 1 of 1

It is certified that error appears in the above-identified patent and that said Letters Patent is hereby corrected as shown below:

On the Title Page

Column 1 (PCT Filed), Line 1, delete "Sep. 8, 2009" and insert -- Sep. 9, 2009 --.

Column 1 (PCT No.), Line 1, delete "PCT/US2009/056229" and insert -- PCT/US2009/056299 --.

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*